(12) United States Patent
Lawrence, III et al.

(10) Patent No.: US 7,256,182 B2
(45) Date of Patent: *Aug. 14, 2007

(54) GENE DELIVERY COMPOSITIONS AND METHODS

(75) Inventors: John H. Lawrence, III, Reisterstown, MD (US); J. Kevin Donahue, Baltimore, MD (US)

(73) Assignee: Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/007,315

(22) Filed: Dec. 9, 2004

(65) Prior Publication Data

US 2005/0101559 A1 May 12, 2005

Related U.S. Application Data

(63) Continuation of application No. 10/092,184, filed on Mar. 5, 2002, now Pat. No. 6,855,701, which is a continuation of application No. 09/169,739, filed on Oct. 8, 1998, now Pat. No. 6,376,471.

(60) Provisional application No. 60/062,018, filed on Oct. 10, 1997.

(51) Int. Cl.
*A61K 48/00* (2006.01)

(52) U.S. Cl. ............... 514/44; 435/320.1; 435/69.1; 435/455; 424/93.2

(58) Field of Classification Search .............. None
See application file for complete search history.

(56) References Cited

U.S. PATENT DOCUMENTS

| 4,438,029 | A | 3/1984 | Erickson et al. | 260/112.5 |
|---|---|---|---|---|
| 5,177,060 | A | 1/1993 | Wei | 514/15 |
| 5,219,746 | A | 6/1993 | Brinegar et al. | |
| 5,240,848 | A | 8/1993 | Keck et al. | |
| 5,308,622 | A | 5/1994 | Casscells et al. | |
| 5,328,470 | A | 7/1994 | Nabel et al. | |
| 5,652,225 | A | 7/1997 | Isner | 514/44 |
| 5,661,133 | A | 8/1997 | Leiden et al. | |
| 5,693,622 | A | 12/1997 | Wolff et al. | |
| 5,776,427 | A | 7/1998 | Thorpe et al. | |
| 5,797,870 | A | 8/1998 | March et al. | |
| 5,853,694 | A | 12/1998 | Engberts et al. | 424/1.21 |
| 5,869,230 | A | 2/1999 | Sukhatme | 435/1.1 |
| 6,007,817 | A | 12/1999 | Epstein et al. | 424/178.1 |
| 6,013,780 | A | 1/2000 | Neufeld et al. | 536/23.1 |
| 6,015,556 | A | 1/2000 | Bagshave | 424/134.1 |
| 6,177,403 | B1 | 1/2001 | Stedman | |
| 6,214,620 | B1 | 4/2001 | Johns et al. | |
| 6,265,387 | B1 * | 7/2001 | Wolff et al. | 514/44 |
| 6,376,471 | B1 * | 4/2002 | Lawrence et al. | 514/44 |
| 6,855,701 | B2 * | 2/2005 | Lawrence et al. | 514/44 |
| 2003/0195495 | A1 * | 10/2003 | Ryan et al. | 606/15 |

FOREIGN PATENT DOCUMENTS

| EP | 0-370989 A2 | 11/1989 |
|---|---|---|
| WO | WO 93/00051 | 1/1993 |
| WO | WO 96/37196 | 11/1996 |

OTHER PUBLICATIONS

Invitrogen life technologies. Calcium Phospahte Transfection Kit and Technical Resources Media Formulations.*
Guzman et al., *Cir Res* 1993, 73:1202-1207.
Kass-Eisler, *Proc Natl Acad Sci* 1993, 90:11498-11502.
Barr et al., *Gene Therapy* 1994, 1:51-58.
Muhlhauser et al., *Gene Therapy* 1996, 3:145-153.
Wang et al., *Transplation* 1996, 61:1726-1729.
Grossman et al., *Nat Genet* 1994, 6:335-341.
Kay et al., *Science* 1993, 262:117-119.
Raper et al., *Cel Transplation* 1993, 2:381-400.
Ferry et al., *Proc Natl Acad Sci USA* 1991, 88:8377-8391.
Lieber et al., *Proc Natl Acad Sci USA* 1995, 92:6210-6214.
Heikkilia et al., *Gene Ther* 1996, 3(1):21-27.
Mastrangelo et al., *Seminars In Oncology* vol. 23, 1996.
Anderson et al., *Nature*, vol. 392, 25-30, 1998.
Verma et al., *Nature*, vol. 389, 239-242, 1997.

* cited by examiner

*Primary Examiner*—Joseph Woitach
*Assistant Examiner*—Maria Leavitt
(74) *Attorney, Agent, or Firm*—Banner & Witcoff

(57) ABSTRACT

The present provides methods and compositions that enable effective delivery of nucleic acids to desired cells, including to a solid organ such as a mammalian heart. The methods and compositions enable effective gene transfer and subsequent expression to a majority of cells throughout a solid organ such as the heart. Methods and compositions of the invention preferably provide enhanced vascular permeability that enables increased gene transfer to targeted cells, but without significant degradation or injury to endothelial cell layers. Global delivery of nucleic acid to an intact heart has been achieved with as little as 2 minutes of intracoronary exposure to the administered nucleic acid.

60 Claims, 3 Drawing Sheets

GENE DELIVERY COMPOSITIONS AND METHODS

CROSS-REFERENCE TO RELATED APPLICATIONS

This application is a continuation of U.S. Ser. No. 10/092,184, filed Mar. 5, 2002, now issued as U.S. Pat. No. 6,855,701, which is a continuation of U.S. Ser. No. 09/169,739, filed Oct. 8, 1998, now issued as U.S. Pat. No. 6,376,471 and claims the benefit of U.S. provisional application Ser. No. 60/062,018, filed Oct. 10, 1997, which is incorporated herein by reference in its entirety.

BACKGROUND OF THE INVENTION

1. Field of the Invention

The present invention relates to improved gene transfer methods and, more particularly, methods that enable highly efficient and widespread delivery of selected nucleic acids, to solid organs such as the heart or liver as well as to other solid cell masses such as a solid tumor.

2. Background

Effective delivery of nucleic acid to cells or tissue with high levels of expression are continued goals of gene transfer technology. As a consequence of the general inability to achieve those goals to date, however, clinical use of gene transfer methods has been limited.

Thus, for example, several delivery schemes have been explored for in vivo myocardial gene transfer, but none has proven capable of modifying a majority of cardiac myocytes in a homogeneous fashion. Techniques involving injection directly into the myocardium are considered of limited use because gene expression does not extend significantly beyond the needle track. R. J. Guzman et al. *Circ Res* 1993; 73:1202-1207; A. Kass-Eisler *Proc Natl Acad Sci* 1993; 90:11498-11502. In one study, percutaneous intracoronary delivery of $10^{10}$ pfu of adenovirus caused infection in only about one-third of the myocytes in the region served by the target artery. E. Barr et al. *Gene Therapy* 1994, 1:51-58.

Other coronary delivery models, either in situ or ex vivo, have produced a very small percentage of infected cells spread throughout the heart. J. Muhlhauser et al. *Gene Therapy* 1996; 3:145-153; J. Wang et al. *Transplantation* 1996; 61:1726-1729. To date, no in vivo delivery system has been able to infect a majority of cells in an intact heart.

Certain gene delivery procedures also have been quite invasive and hence undesirable. For example, one report describes essentially complete loss of endothelium by mechanical or proteolytic means to enable gene transfer from blood vessels to cells positioned across interposing endothelial layers. See WO 93/00051.

Certain gene transfer applications also have been explored in other organs such as the liver. In particular, ex vivo strategies have included surgical removal of selected liver cells, genetic transfer to the cells in culture and then reimplantion of the transformed cells. See M. Grossman et al., *Nat Genet* 1994, 6:335-341. Such an ex vivo approach, however, suffers from a number of drawbacks including, for example, the required hepatocyte transplantation. M. A. Kay et al., *Science* 1993, 262:117-119; and S. E. Raper et al., *Cell Transplant* 1993, 2:381-400. In vivo strategies for gene transfer to the liver also have been investigated, but have suffered from low delivery efficiencies as well as low specificity to the targeted tissue. N. Ferry et al., *Proc Natl Acad Sci USA* 1991, 88:8377-8391; A. Lieber et al. *Proc Natl Acad Sci USA* 1995, 6:6230-6214; A. L. Vahrneijer et al., *Reg Cancer Treat* 1995, 8:25-31. See also P. Heikkilia et al., *Gene Ther* 1996, 3(1):21-27.

Gene transfer has been generally unsuccessful in additional applications. For example, gene transfer therapies for treatment of cystic fibrosis have largely failed because transduction of insufficient numbers of cells.

It thus would be desirable to have improved methods and systems to effectively deliver nucleic acid to targeted cells and tissue. It would be particularly desirable to have new methods and systems for effective delivery of nucleic acids into solid organs, especially the heart, liver, lung and the like, as well as other solid cell masses such as a solid tumor.

SUMMARY OF THE INVENTION

We have now found methods and compositions that enable effective delivery of nucleic acids to desired cells, including to a solid mass of cells, particularly a solid organ such as a mammalian heart, liver, kidney, skeletal muscle, spleen or prostate, or to malignant cells such as a solid tumor. These methods and compositions enable effective gene transfer and subsequent expression of a desired gene product to a majority of cells throughout a solid cell mass, and/or gene transfer and subsequent expression of a desired gene product to a solid cell mass in a desired percentage of total cells of the mass, including up to nearly 100% of targeted cells of the mass. For example, using methods and compositions of the invention, greater than 90 percent of total cardiac myocytes showed expression of nucleic acid that was perfused for two minutes through an intact rabbit heart.

Methods and compositions of the invention preferably provide enhanced vascular permeability that enables increased nucleic acid delivery to targeted cells. While not being bound by theory, it is believed these methods and compositions of the invention induce transient permeability or interruption of endothelial layers to thereby enhance gene transfer efficiency. This is distinguished from prior approaches that significantly degraded or injured endothelial cell layers in attempts to administer nucleic acid.

Such enhanced permeability can be readily accomplished by one of several alternative approaches, or by a combination of strategies. A preferred approach provides for use of a vasculature permeability agent. As demonstrated in the Examples which follow, use of a suitable permeability agent significantly enhances transfer of administered nucleic acid to targeted cells. A permeability agent suitably may be administered through the vasculature of targeted tissue prior to administration of nucleic acid, and/or the permeability agent and exogenous nucleic acid can be administered simultaneously. Preferably, the vasculature of targeted tissue is pre-treated with a permeability agent.

Preferred vasculature permeability agents include serotonin and bradykinin. Other suitable permeability agents will include platelet-activating factor (PAF), prostaglandin $E_1$ ($PGE_1$), histamine, vascular endothelium growth factor (VEGF), zona occludens toxin (ZOT), interleukin-2 and other plasma kinins in addition to bradykinin. Nitric oxide inhibitors, e.g. L-N-monomethyl arginine (L-NMMA) and L-N-nitro-arginine methyl ester (L-NAME), also can provide suitable results, although these agents may be less preferred than others such as serotonin and bradykinin. Other suitable agents can be readily identified, e.g. simply by testing a candidate permeability agent to determine if it enhances uptake of nucleic acid by targeted tissue relative to a control tissue sample that has not been exposed to the candidate permeability agent. A single or a combination of more than one distinct permeability agents may be administered in a particular application. In this regard, a particular application can be optimized by selection of an optimal permeability agent, or optimal "cocktail" of multiple permeability agents. Such optional agent(s) can be readily identified by those skilled in the art by routine procedures, e.g. testing selected permeability agents and combinations thereof in in vivo assays.

Low extracellular calcium ion concentration conditions also can be used to enhance vascular permeability. It has been found that transfer of administered nucleic acid to targeted cells is substantially enhanced under such conditions, which also is demonstrated in the Examples which follow. Low calcium concentration conditions may be readily provided, particularly by perfusing a low calcium ion concentration fluid through the vasculature of the tissue to which nucleic acid is administered. Suitable perfusate calcium ion concentrations may range from about 40 or 50 µmol/L to about 500 µmol/L, more preferably from about 50 µmol/L to about 200 µmol/L. A perfusate calcium concentration of about 50 µmol/L is particularly preferred. Calcium ion (e.g. $Ca^{2+}$) concentration also can be lowered through use of a suitable buffer such as a chelating agent, e.g. ethylenebis(oxyethylenenitrilo)tetracetic acid (EGTA), ethylenediaminetetracetic acid (EDTA), or 1,2-bis-(2-aminophenoxy)ethane-N,N,N',N'-tetraacetic acid (BAPTA).

Additionally, while a low calcium ion concentration can enhance nucleic acid uptake, it is also important that a minimal calcium concentration be maintained during the gene transfer protocol, at least in many or some applications. If calcium-free or essentially calcium-free conditions (e.g. perfusate calcium ion concentration of about 10-20 µmol/L or less) are employed, cell calcium channel selectivity may be destroyed which can result in cell death upon return to physiological calcium levels, particularly in the case of administration to myocytes.

We have also found that combined use of a vasculature permeability agent and low calcium ion concentration conditions appears to provide synergistic results with higher gene transfer efficiency than that provided with either use of a permeability agent without a lowered calcium concentration, or low calcium concentration conditions in the absence of a permeability agent. Thus, as discussed above and demonstrated in the Examples which follow, greater than 90 percent of rabbit total cardiac myocytes showed expression of nucleic acid that was perfused for two minutes through an intact rabbit heart under low calcium ion concentration conditions and treatment with a permeability agent.

We also have found that certain administration conditions in addition to those discussed above also will impact efficiency of nucleic acid uptake by targeted tissue. In particular, concentration, amount and exposure time of the administered nucleic acid and temperature of the targeted tissue all can effect the rate of gene transfer. Flow rate and perfusion pressure also can effect the rate of gene transfer.

More specifically, in a perfusion administration protocol, the rate of gene transfer increases with increase in concentration, total amount and exposure time of the administered nucleic acid in a perfusate. High concentration of nucleic acid in a perfusate especially can increase gene transfer rate. Preferred perfusate concentrations can vary with a number of factors including the particular organ or cell mass being treated, the particular cloning vehicle being administered and the like. However, in general, preferred concentrations of a viral vector in an administered perfusate are about $1 \times 10^8$ pfu/ml or greater, more preferably a concentration of about $5 \times 10^8$ pfu/ml or greater. Administered perfusate also preferably may be recirculated and readministered to a subject, e.g. to limit the total viral burden introduced into the target, or if the administered agent is in short supply. However, effective gene transfer can be achieved without recirculation, particularly if other delivery parameters are optimized. Increases in either flow rate of perfusate pressure generally will increase gene transfer efficiency, although for clinical safety it can be desirable to limit both perfusate pressure and flow rate.

The rate of gene transfer also decreases with decreased temperature of targeted tissue, particularly where the tissue is below about 20° C. Delivery of the nucleic acid near body temperature of the subject is preferred, e.g. where the nucleic acid is administered at a temperature of from about 28-45° C., more preferably from about 34-40° C. However, gene transfer can be achieved over wide temperature ranges, e.g. at about 4° C. Clinical circumstances may require lower temperatures, e.g. with gene transfer during cardiac surgery.

Nucleic acid administered in accordance with the invention can express a desired therapeutic agent, or may inhibit expression or function of an endogenous gene of a subject. Nucleic acid also may be administered for diagnostic purposes, for example to express a marker protein. In addition to such therapeutic and diagnostic methods, methods and compositions of the invention also may be employed to examine the effect of a heterologous gene on an intact organ such as a subject's heart, to create animal models of disease and to provide mechanistic information regarding various disease states.

In a preferred aspect, the invention includes methods for xenotransplantation. Thus, for example, cells of xenogeneic tissue, particularly cells of a xenogeneic solid cells mass, can be administered exogenous nucleic acid under enhanced vascular permeability as described herein. Those cells containing exogenous nucleic acid then may be transplanted into a subject. More particularly, the exogenous nucleic acid can be administered in vivo or ex vivo to donors cells or organs, e.g. a xenogeneic heart, liver, spleen and the like, in accordance with the invention and the donor cells or organ can be transplanted to a selected host, e.g. a mammal, particularly a primate such as a human. Suitable donor organs may be obtained from e.g. another primate, or a swine, particularly a pig. A variety of exogenous nucleic acids can be administered to the donor cells. For instance, nucleic acids can be administered that will express a gene product that can promote a desired phenotypic characteristic. Exemplary gene products include those which can reduce immune system recognition of the xenotransplanted cells.

In another aspect, the invention includes vasculature permeability and gene transfer solutions useful in the methods of the invention. Such solutions in general will be formulated to provide enhanced permeability to treated tissue upon administration of nucleic acid to such layers. Thus, suitable permeability agents will include one or more permeability agents as disclosed herein, or otherwise may be formulated to enhance permeability such as a low calcium ion concentration solution as described herein. A solution of the invention also may contain one or more therapeutic agents, e.g. one or more exogenous nucleic acids (e.g. one or more recombinant adenoviruses) to be administered to a subject, or other pharmaceutical agent such as nitroglycerine to control vasospasms and the like to a solution that will be administered to a heart. A permeability or gene transfer solution may suitably contain nucleic acid in a form for administration e.g. in a suitable cloning vehicle such as a viral vector dissolved in desired pharmaceutically acceptable carrier e.g. Krebs solution or other buffered solution. A permeability or gene transfer solution of the invention preferably will be pharmaceutically acceptable, e.g. sterile and otherwise suitable for administration to a subject. Typically a vasculature permeability or gene transfer solution will be stored in a sealed (preferably, hermetically sealed) container prior to use. A permeability or gene transfer solution preferably will contain active ingredients (i.e., permeability agent, calcium ion concentration, nucleic acid) in optimal dosage quantities. Solutions of the invention may suitably have other agents such as various buffers, sugars, salts and the like.

A wide variety of cells may be treated in accordance with the invention. Suitable cells for administration include those that have a distinct circulation, or circulation that can be isolated in some manner. Thus, for example, organs and other cell masses are suitable for administration in accordance with the invention including e.g. heart, lung, liver, kidney, prostrate, testes, ovaries, skeletal muscle, kidneys, brain, spleen and solid tumors. Exemplary tumors that can be treated in accordance with the invention include e.g. cancers of the lung, prostate, liver, brain, testes or ovaries. Cells treated in accordance with the invention may be in either a healthy or diseased state. A wide variety of subjects also may be treated in accordance with the invention. Typical subjects include mammals, particularly primates, especially humans.

Other aspects of the invention are discussed below.

DETAILED DESCRIPTION OF THE INVENTION

Figure 1A:
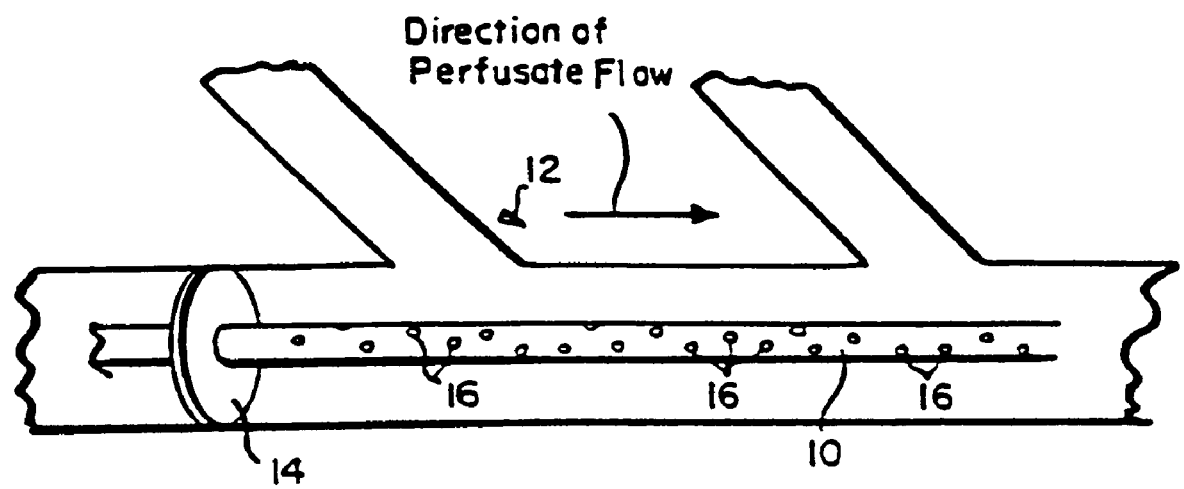
FIG. 1A shows schematically a perfusion catheter suitable for in vivo nucleic acid administration to a heart in accordance with the invention.

As stated above, the present invention provides methods and compositions that enable effective delivery of nucleic acid to desired cells, including to cells of a solid cell mass, e.g. of an organ such as a mammalian heart or liver, or other solid cell mass such as a solid tumor.

Preferably, the methods and compositions of the invention provide enhanced microvascular permeability that enables increased gene transfer to targeted cells. As discussed above, these methods and compositions create transient permeability of endothelial layers, and preferably without significant degradation or injury to endothelial cell layers of a solid cell mass, although some transient disruption of the endothelial layer may occur.

As used herein, the term "without significant degradation or injury to endothelial cell layers" or other similar phrase means that less than 25%, more typically less than 15 or 10 percent, of endothelial cells are lost from the treated vessel wall prior to administration of nucleic acid to a subject. This contrasts from denuding and consequent injury of the endothelium through mechanical trauma or use of proteolytic enzymes which would result through use of prior methods. Lack of significant degradation of endothelial cell layers can be readily determined, e.g. by microscopic examination of the layer. Also, lack of significant degradation of endothelial cell layers can be determined by simple testing. For example, an endothelial layer can be tested to determine whether the layer has maintained a particular function and therefore is significantly degraded, e.g. a layer's ability to exhibit a reversible vasodilator response to $10^{-7}$ mol/L acetylcholine.

As discussed above, a wide variety of agents will be suitable as permeability agents in accordance with the invention, and that suitably of a particular candidate permeability agent can be readily evaluated by testing the agent to determine if the candidate agent enhances uptake of nucleic acid by targeted tissue relative to a control tissue sample that has not been exposed to the candidate permeability agent. For example, a candidate permeability suitably may provide at least about 10, 20, 30, 40, 50, 60, 70, 80 or 90 percent greater uptake of nucleic acid by targeted tissue relative to a control tissue sample that has not been exposed to the candidate permeability agent. In certain applications, use of a permeability agent having even greater uptake of nucleic acid may be preferred, e.g. where the permeability agent provides at least about 100, 125, 150, 175, 200, 300, 400, 500, 600, 800 or 1000 percent greater uptake of nucleic acid by targeted tissue relative to a control tissue sample that has not been exposed to the permeability agent. It also should be appreciated that the level of nucleic agent uptake that will be suitable for various applications can differ. Thus, for certain applications, lower levels of nucleic acid uptake (e.g. nucleic acid uptake in 2% of cells in a target organ or mass of cells) may be suitable for one application, whereas for other applications, higher levels of nucleic acid uptake (e.g. nucleic acid uptake approaching 90 or 100% of cells in a target organ or mass of cells) may be optimal; The conditions herein described enable graded levels of nucleic acid uptake, e.g. by appropriate varying of type and quantity of permeability agent, virus amount or concentration, and virus exposure time.

Suitable permeability agents generally will exhibit good activity in a standard in vitro vasculature permeability assay. For example, permeability agents preferred for at least many applications will include those compounds that exhibit at least about 5%, more preferably at least about 10%, still more preferably at least about 25% or 50% of the permeability activity exhibited by an equivalent molar concentration of bradykinin in a standard vasculature permeability assay, specifically the assay disclosed in R. J. Mullins et al., *Journal of Trauma* 1989, 29(6):1053-1063. That disclosed assay includes measuring skin lymph flow (LYM FLOW μl/min) after perfusing a solution containing the permeability agent through specified vasculature of a test animal for a specified period of time. References herein to a standard permeability assay are intended to refer to that protocol and as disclosed in R. J. Mullins, supra.

It also should be appreciated that optimal permeability agents and conditions for a particular application may vary with a number of factors such as the specific nucleic acid being administered, the solid cell mass that is being treated and the like. Thus, while histamine may be suitable for many applications of the invention, histamine may be less suitable for certain applications and is excluded from certain aspects of the invention. Again, the suitably of any particular agent can be readily determined by simple testing as discussed above.

Nucleic acid administered in accordance with the invention may be any nucleic acid (DNA or RNA) including genomic DNA, cDNA, rRNA, mRNA and tRNA. These constructs may encode a gene product of interest, e.g. a therapeutic or diagnostic agent. A wide variety of known polypeptides are known that may be suitably administered to a patient in accordance with the invention.

For instance, for administration to cardiac myocytes, nucleic acids that encode vasoactive factors may be employed to treat vasoconstriction or vasospasm. Nucleic acids that encode angiogenic growth factors may be employed to promote revascularization. Suitable angiogenic growth factors include e.g. the fibroblast growth factor (FGF) family, endothelial cell growth factor (ECGF) and vascular endothelial growth factor (VEGF; see U.S. Pat. Nos. 5,332,671 and 5,219,739). See Yanagisawa-Miwa et al., *Science* 1992, 257:1401-1403; Pu et al., *J Surg Res* 1993, 54:575-83; and Takeshita et al., *Circulation* 1994, 90:228-234. Additional agents that may be administered to ischemic heart conditions, or other ischemic organs include e.g. nucleic acids encoding transforming growth factor α (TGF-α), transforming growth factor β (TGF-β), tumor necrosis factor α and tumor necrosis factor β. Suitable vasoactive factors that can be administered in accordance with the invention include e.g. atrial natriuretic factor, platelet-derived growth factor, endothelin and the like. Additional agents that may be administered for the prevention of atrial or ventricular arrhymias include ion channel proteins and/or functionally effective subunits and/or fragments of ion channel proteins that can function to either overexpress or inhibit certain ion currents in the hearts. Further regulatory sequences, such as promoter elements may be added to restrict expression to specific regions of an organ, such as the heart (e.g., atrial natriuretic factor promoter produces preferential expression in the atria relative to the ventricles). Alternatively, regulatory sequences may be added so that expression is regulated up or down by an administered or endogenous compound, such as a hormone.

For treatment of malignancies, particularly solid tumors, nucleic acids encoding various anticancer agents can be employed, such as nucleic acids that code for diphtheria toxin, thymidine kinase, pertussis toxin, cholera toxin and the like. Nucleic acids encoding antiangiogenic agents such as matrix metalloproteases and the like also can be employed. See J. M. Ray et al. *Eur Respir J* 1994, 7:2062-2072.

For other therapeutic applications, polypeptides transcribed by the administered nucleic acid can include growth factors or other regulatory proteins, a membrane receptor, a structural protein, an enzyme, a hormone and the like.

Also, as mentioned above, the invention provides for inhibiting expression or function of an endogenous gene of a subject. This can be accomplished by several alternative approaches. For example, antisense nucleic acid may be administered to a subject in accordance with the invention. Typically, such antisense nucleic acids will be complementary to the mRNA of the targeted endogenous gene to be suppressed, or to the nucleic acid that codes for the reverse complement of the endogenous gene. See J. H. Izant et al., *Science* 1985, 229:345-352; and L. J. Maher II et al., *Arch Biochem Biophys* 1987, 253:214-220. Antisense modulation of expression of a targeted endogenous gene can include antisense nucleic acid operably linked to gene regulatory sequences.

Alternatively, nucleic acid may be administered which antagonizes the expression of selected endogenous genes (e.g. ribozymes), or otherwise interferes with function of the endogenous gene or gene product.

The nucleic acid to be administered can be obtained by known methods, e.g. by isolating the nucleic acids from natural sources or by known synthetic methods such as the phosphate triester method. See, for example, Oligonucleotide Synthesis, IRL Press (M. J. Gait, ed. 1984). Synthetic oligonucleotides also may be prepared using commercially available automated oligonucleotide synthesizers. Also, as is known, if the nucleic acid to be administered is mRNA, it can be readily prepared from the corresponding DNA, e.g. utilizing phage RNA polymerases T3, T7 or SP6 to prepare mRNA from the DNA in the presence of ribonucleoside triphosphates. The nucleotide sequence of numerous therapeutic and diagnostic peptides including those discussed above are disclosed in the literature and computer databases (e.g., GenBank, EMBL and Swiss-Prot). Based on such information, a DNA segment may be chemically synthesized or may be obtained by other known routine procedures such as PCR.

To facilitate manipulation and handling of the nucleic acid to be administered, the nucleic acid is preferably inserted into a cassette where it is operably linked to a promoter. The promoter should be capable of driving expression in the desired cells. The selection of appropriate promoters can be readily accomplished. For some applications, a high expression promoter is preferred such as the 763-base pair cytomegalovirus (CMV) promoter. The Rous sarcoma (RSV) (Davis et al., *Hum Gene Ther,* 1993, 4:151) and MMT promoters also may be suitable. Additionally, certain proteins can be expressed using their native promoter. Promoters that are specific for selected cells also may be employed to limit transcription in desired cells. Other elements that can enhance expression also can be included such as an enhancer or a system that results in high expression levels such as a tat gene or a tar element. A cloning vehicle also may be designed with selective receptor binding and using the promoter to provide temporal or situational control of expression.

The cassette then can be inserted into a vector, e.g. a viral vector such as adenoviruses, adeno-associated virus, retroviruses, herpes viruses (e.g. herpes simplex virus), vaccina viruses, papoviruses, the Sendai virus, the SV40 virus, hybrid viruses, and the like. As mentioned above, adenoviruses are generally preferred. Lytic and semi-lytic viral vectors also can be employed, particularly for administration to malignant cells, such as cells of a solid tumor. Replication-defective recombinant adenoviral vectors, and other suitable vectors, can he produced by known procedures. See Quantin et al., *Proc Natl Acad Sci USA* 1992, 89:2581-2584; Stratford-Perricadet et al., *J. Clin. Invest.* 1992, 90:626-630; and Rosenfeld et al., *Cell* 1992, 68:143-155. The vector also may contain a selectable marker, for instance β-galactosidase (β-gal) or GFP as employed in the Examples which follow. In general, preparation of vector containing desired nucleic acid for administration to a subject is in accordance with known procedures as disclosed e.g. in Molecular *Cloning, A Laboratory Manual* (2d ed., Sambrook, Fritsch and Maniatis, Cold Spring Harbor 1989); *Current Protocols in Molecular Biology*, (eds. Aufubel et al., Greene Publ. Assoc., Wiley-Interscience, NY, N.Y. 1992); and *Methods in molecular biology* (ed. E J Murray, Humana, Clifton, N.J. 1991). See also the Examples which follow for exemplary procedures.

Naked nucleic acid also may be administered in accordance with the invention, typically formulated with a pharmaceutically acceptable carrier. For example, a polynucleotide, optionally present as a pharmaceutically acceptable salt, can be present in forms such as suspensions, solutions, emulsions in oily or preferably aqueous vehicles that are preferably sterile and pyrogen-free. Pharmaceutically acceptable salts can be suitably prepared from organic or inorganic bases, such as a sodium or potassium salt, or a salt of a primary, secondary or tertiary amine. The administration solution can suitably contain buffers to adjust the pH of the solution, nonionic materials such as sugars e.g. sucrose to adjust tonicity.

Nucleic acid also may be administered as DNA-liposome or RNA-liposome complexes. Such complexes comprise a mixture of fat particles or lipids which bind to DNA or RNA to provide a hydrophobic coated delivery vehicle. Suitable liposomes may comprise any of the conventional synthetic or natural phospholipid liposome materials including phospholipids from natural sources such as egg, plant or animal sources such as phosphatidylcholine, phosphatidylethanolamine, phosphatidylglycerol, sphingomyelin, phosphatidylserine or phosphatidylinositol. Synthetic phospholipids also may be used e.g., dimyristoylphosphatidylcholine, dioleoylphosphatidylcholine, dioleoylphosphatidycholine and corresponding synthetic phosphatidylethanolamines and phosphatidylglycerols. Cholesterol or other sterols, cholesterol hemisuccinate, glycolipids, 1,2-bis(oleoyloxy)-3-(trimethyl ammonio)propane (DOTAP), N-[1-(2,3-dioleoyl) propyl]-N,N,N-trimethylammonium chloride (DOTMA), and other cationic lipids may be incorporated into the liposomes.

Typical subjects to which nucleic acid will be administered for therapeutic application include mammals, particularly primates, especially humans, and subjects for xenotransplant applications such as a primate or swine, especially pigs. For veterinary applications, a wide variety of subjects will be suitable, e.g. livestock such as cattle, sheep, goats, cows, swine and the like; poultry such as chickens, ducks, geese, turkeys and the like; and pets such as dogs and cats. For diagnostic or research applications, a wide variety of mammals will be suitable subjects including rodents (e.g. mice, rats, hamsters), rabbits, primates, and swine such as inbred pigs and the like.

The effective dose of nucleic acid will be a function of the particular expressed protein, the target tissue, the subject (including species, weight, sex, general health, etc.) and the subject's clinical condition. The effective dose of nucleic acid also will be a function of the permeability cocktail, which generally will allow less total viral particles to be delivered. Optimal administration rates for a given protocol of administration can be readily ascertained by those skilled in the art using conventional dosage determination tests. Additionally, frequency of administration for a given therapy can vary, particularly with the time cells containing the exogenous nucleic acid continue to produce the desired polypeptide as will be appreciated by those skilled in the art. Also, in certain therapies, it may be desirable to employ two or more different proteins to optimize therapeutic results.

Nucleic acid can be administered to selected tissue by a variety of protocols. The preferred administration method is perfusion of a liquid formulation of the nucleic acid through a solid organ such as a heart or liver or other solid cell mass such as a solid tumor. It may be preferred to recirculate the perfusate through the organ or cell mass which, among other things, can limit delivery of the nucleic acid to targeted cells. A preferred perfusion protocol is described in the Examples which follow. See also Donahue et al., *Proc Natl Acad Sci USA* 1997, 94:4664-4668 for suitable perfusion procedures.

If an adenovirus vector is employed, the nucleic acid preferably is administered in a formulation that is essentially (less than about 5 percent by volume) or completely free of red blood cells which can adsorb adenovirus. Krebs solution is a particularly preferred carrier. Preferably the liquid carrier has a low calcium ion concentration as discussed above. However, other solutions, even native bloodstream with physiologic levels of red blood cells and calcium, can be employed and may be suitable for certain applications, e.g. where the primary intervention for enhancing gene transfer is alteration of vascular permeability.

The concentration of nucleic acid within a liquid carrier can vary, but relatively high concentrations are preferred to provide increase efficiency of nucleic acid uptake as discussed above. More specifically, preferably a viral vector containing nucleic acid for administration is present in a liquid carrier such as Krebs solution at a concentration of about $1 \times 10^8$ plaque forming units (pfu)/ml or greater, more preferably a concentration of about or $5 \times 10^8$, still more preferably a concentration of about $1.0 \times 10^9$ or $1.5 \ 10^9$ pfu/ml or greater.

Flow rates of a perfusate solution containing nucleic acid also can vary, but are preferably relatively rapid compared to normal blood flow in the delivery vessel to provide enhanced nucleic acid uptake. For example, a perfusate flow rate of at least about 5, 10, 15, 20, 25, 50 or 75 percent more rapid compared to normal blood flow in the delivery vessel can be employed. In certain applications, even more rapid flow rates will be preferred, e.g. a perfusate flow rate of at least about 100, 200, 300, 400 or 500 percent more rapid compared to normal blood flow. Flow rates up to 600, 700, 800, 900 or 1000 percent more rapid compared to normal blood flow rate of a subject also can be suitable for certain applications.

It should be appreciated that a particular application of the invention can be readily optimized, e.g. the optimal permeability agents readily selected as discussed above by simple testing against a control; the use of lowered calcium conditions can be readily assessed by testing relative to a control; perfusate flow rates, perfusate concentrations of nucleic acids and the like also all can be readily optimized by testing relative to a control. Optimal conditions and agents may vary from application to application, e.g. for administration to varying organs or mammals of different species.

Nucleic acid can be administered by perfusion by a variety of strategies. Thus, for instance, for an in vivo administration, a catheter delivery protocol can be employed. Such in situ administration can be suitably employed in a procedure solely to deliver the nucleic acid, or in conjunction with a separate surgical procedure such as a peripheral cardiac bypass.

FIG. 1A of the drawings depicts perfusion catheter 10 which can be suitably used for an in vivo administration. In use, catheter 10 can be inserted into selected delivery vessel of a subject such as the depicted mammalian heart 12. The catheter balloon 14 that occludes blood flow, thereby preventing mixing of red blood cells with the perfusate, and defines a point at which administered perfusate enters the selected vasculature via multiple perfusion openings 16. As should be clear, the administered perfusate can be a number of compositions, such as a solution containing on or more permeability agents, a low calcium ion concentration "wash-out" solution or a solution containing nucleic acid. The isolation provided by balloon 14 can prevent backflow of perfusate to vascular beds proximal to balloon 14. If the venous circulation is not collected, then the perfusate may spread more widely in the body. If desired, the administered solutions may be recirculated through the catheter system and then readministered to the delivery vessel of the subject. Direction of flow through the catheter system is shown by the depicted arrow in FIG. 1A. As is known in the art, the catheter can be advanced to an area of treatment of a subject with a guide wire and use of radiopaque markers.

Figure 1B:
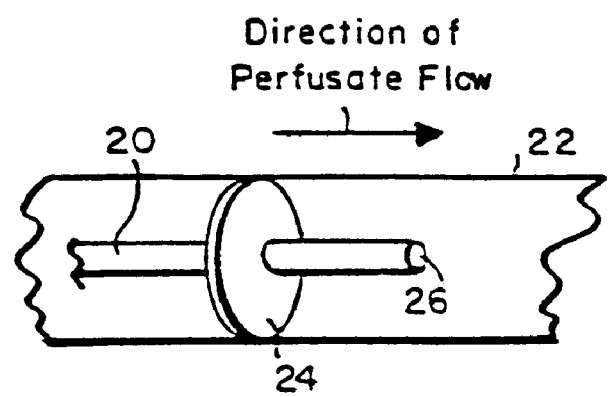
FIG. 1B shows schematically an alternate catheter suitable for in vivo nucleic acid administration to a heart in accordance with the invention.

FIG. 1B of the drawings depicts a further catheter 20 which also can be suitably used for an in vivo administration. In use, catheter 20 can be inserted into selected delivery vessel 22 of a subject such as a mammalian heart. As with catheter 10, catheter balloon 24 defines a point at which administered perfusate enters the selected vasculature through end lumen or opening 26. As again with catheter 10, perfusate administered with catheter 20 can be a number of compositions, such as a solution containing on or more permeability agents, a low calcium ion concentration "washout" solution or a solution containing nucleic acid. Isolation provided by balloon 24 prevents spread of the nucleic acid to other areas other than the targeted cell mass. If desired, the administered solutions may be recirculated through the catheter system and then readministered to the delivery vessel of the subject. Direction of flow through the catheter system is shown by the depicted arrow in FIG. 1B. Catheter 20 also can be advanced to an area of treatment of a subject with a guide wire and use of radiopaque markers.

Nucleic acid also may be suitably administered by perfusion through a procedure involving extra-corporal circulation such as performed during coronary artery bypass surgery and aortic valve replacement surgery. In such clinical settings, both arterial and venous vessels can be accessed for delivery, collection and possible recirculation of the perfusate formulation thus targeting gene transfer to the heart and minimizing delivery to remote organs or tissues.

Figure 2:
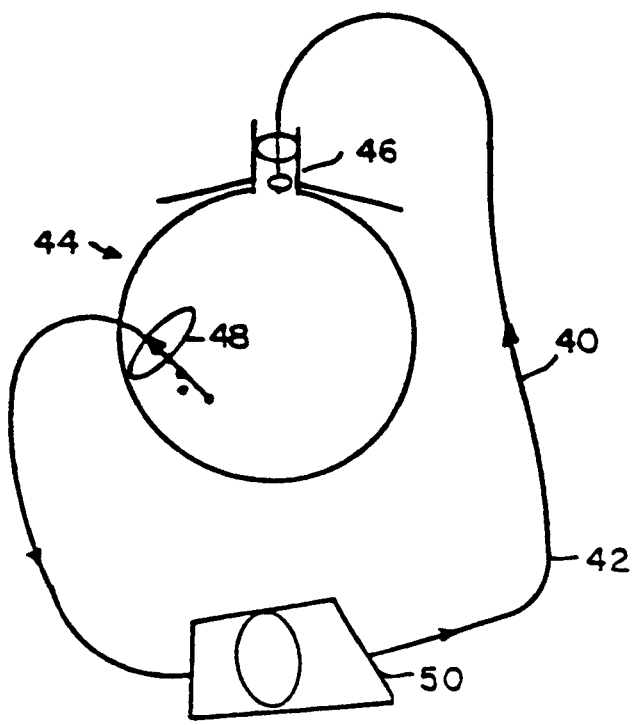
FIG. 2 shows schematically an ex vivo cardiac perfusion system in accordance with the invention.

Ex vivo perfusion systems also may be employed, particularly in test animals such as a rabbit, rodent, etc. to assess viability and efficiency of specific permeability agents, calcium concentration conditions, cloning vehicles, and perfusion conditions such as flow rate, amount of nucleic acid administered, concentration of nucleic acid in perfusate, etc. An ex vivo procedure also can be employed to deliver therapeutic procedures followed by transplanted of the organ into a patient. A suitable ex vivo system is shown schematically in FIG. 2 of the drawings and corresponds to the system employed in the Examples. As depicted in FIG. 2, desired fluid 40 (e.g., fluid containing one or more permeability agents, or a calcium "washout" solution, or fluid containing the selected nucleic acid) can be circulated through line 42 and into an explanted organ such as the depicted heart 44. Fluid 40 enters explanted organ 44 through inlet port 46, circulates through and then exits organ 44 via outlet port 48. Fluid 40 can be added or removed through the system, flow rate controlled and the like via automated delivery device 50. Nucleic acid delivery also can be achieved following placement of the balloon catheter within one of the main coronary arteries or branches of the coronary arteries.

Alternate ex vivo methods do not involve removal of an intact organ, but rather removal of selected tissue of an organ followed by reimplanting of the tissue after transformation of the removed cells with the desired exogenous nucleic acid. However, as discussed above, such an approach is generally less preferred for the substantial surgical intervention required and difficulty of effective grafting of genetically modified cells.

Additionally, other therapeutic agents, including non-peptide therapeutics, can be administered together with the gene product of the exogenous nucleic acid. Thus, as one example, nitroglycerine may be co-administered to control vasospasms, or an anticancer agent may be co-administered during treatment of malignant cells.

The invention also provides pharmaceutical kits for treatment of a disorder of a subject. Kits of the invention preferably include a delivery system or device to administer the exogenous nucleic acid such as a catheter as discussed above, an ex vivo administration system such as those discussed above, a syringe for injection administration and the like. The kits also will include the nucleic acid to be administered, preferably in a form suitable for administration, e.g. contained in a suitable cloning vehicle such as a viral vector dissolved in desired pharmaceutically acceptable carrier e.g. Krebs solution or other buffered solution that preferably has a low calcium concentration in accordance with the invention and may have other agents such as various buffers, sugars, salts and the like. Alternatively, the nucleic acid may be freeze dried and packaged separately from the fluid carrier. Preferably the nucleic acid and carrier would be present in the kit in optimal dosage quantities. A pharmaceutical kit of the invention also may contain other therapeutic agents that may be co-administered with the gene product of the exogenous gene product as discussed above.

A kit of the invention also preferably contains one or more vasculature permeability agents, packaged either separately from or admixed with a liquid formulation to perfuse the one or more agents through a selected area of a subject. The kit also may contain a calcium "washout" formulation to lower the calcium concentration to a desired level in a selected area of a subject. For example, such a "washout" solution could be Krebs solution or other fluid having a low calcium concentration in accordance with the invention and administered prior to administration of the exogenous nucleic acid as discussed above. The one or more permeability agents also may be present in the kit either packaged separately from for later formulation, or pre-formulated with such a low calcium concentration solution for administration prior to delivery of the exogenous nucleic acid. Each of the materials of a kit of the invention, or any composition of the invention that is administered to a subject, particularly a human, should be sterile and otherwise pharmaceutically acceptable. Each of the kit materials intended for administration typically will be stored in a suitable container, preferably each such container hermetically sealed. The kit also suitably may contain instructions for use and administration of the kit materials.

As discussed above, the invention also provides methods for introducing into a recipient subject transformed donor cells to express a desired gene product in the recipient. Nucleic acid is introduced into the donor cells in accordance with the invention as described herein, i.e. by enhancing vasculature permeability to introduce desired nucleic acid into the cells. Typical recipient subjects for these xenotransplant methods include those subjects disclosed above, i.e. mammals, particularly primates, preferably a human. Donor cells can come from a variety of sources such as from the sources disclosed above. Donor cells from a swine such a pig, or a primate such as a human, are generally preferred. A solid donor organ containing cells comprising exogenous nucleic acid may be transplanted into the recipient subject. Xenotransplant procedures in general have described in the literature such as in U.S. Pat. Nos. 5,650,148 and 5,658,564 and the like.

All documents mentioned herein are incorporated herein by reference.

The following non-limiting examples are illustrative of the invention.

General Comments

The following materials and conditions were employed in the following Examples 1 and 2.

Adenovirus vectors. Adβgal contained the *E. coli* lac Z gene driven by the human cytomegalovirus (CMV) immediate early promoter. Virus stocks were expanded as previously described in Graham F L, Prevec L: Manipulation of adenovirus vectors, in Murray E J (ed): *Methods in molecular biology*. Clifton, N.J., Humana, 1991, pp 109-128, aliquoted in small volumes, and stored in phosphate-buffered saline (PBS) with 10% sucrose at −80° C. Viral titers were determined by the average of two plaque assays performed using a traditional method as described in *Methods in molecular biology*, supra.

Statistical Analysis. Unless otherwise stated, all experiments were performed in triplicate and the data are presented as mean ±s.d. Statistical significance was determined at the 5% level using the unpaired Student's t-test.

Baseline conditions for the Langendorff-perfusion experiments included a coronary flow rate of 30 ml/min, and perfusion with Krebs solution containing 1.0 mmol/L $Ca^{2+}$ and $1.0 \times 10^8$ pfu/ml of Adβgal at 37° C. All infections occurred in Krebs solution.

EXAMPLE 1

Separate Use of Permeability Agents and Low Calcium Concentration Conditions

Acutely explanted rabbit heart (New Zealand White; 2-3 kg total body weight) were employed for gene transfer tests of this Example 1 and the following Example 2. The rabbits received heparin anticoagulation (1000 units IV) prior to pentobarbital (50 mg/kg IV). Each heart was extracted and rinsed twice in ice-cold, modified Krebs buffer containing 138.2 mM $Na^+$, 5.4 mM $K^+$, 1.2 mM $Mg^{2+}$, 1.0 mM $Ca^{2+}$, 144.4 mM $Cl^-$, 1.2 mM $SO_4^{2-}$, 1.2 mM $H_2PO_4^-$, 20 mM HEPES, and 15 mM glucose, saturated with $O_2$ at pH 7.4. Next, the aorta was cannulated, and the heart was suspended in an insulated chamber at 35-37° C.

Langendorff perfusion occurred by retrograde flow from the cannula in the ascending aorta to the coronary arteries. Each heart was first perfused with 20 ml Krebs buffer at approximately 30 ml/min. After initial perfusion, the heart was pretreated with one of the following: (1) 90 ml of 50 μM calcium-Krebs over 3 minutes, or (2) 500 ml of normal Krebs buffer containing $10^{-5}$ M of either bradykinin or serotonin over 15 minutes.

Following pretreatment, the heart was infected with Krebs buffer containing the pretreatment supplements (i.e. low calcium, serotonin, bradykinin solutions) in the same concentrations and solutions that were employed for pretreatment, 1 mg/ml albumin and Adβgal at specified concentrations. At the end of the infection interval, the virus-containing media was removed and the heart was perfused with virus-free Krebs buffer at a flow rate of 10-30 ml/min to maintain a total Langendorff-perfusion time of 180 minutes before perfusion with nominally calcium-free Krebs and cell isolation by proteolytic digestion. The cells were cultured for 48 hours prior to fixation and staining to detect β-galactosidase activity.

Figure 3:
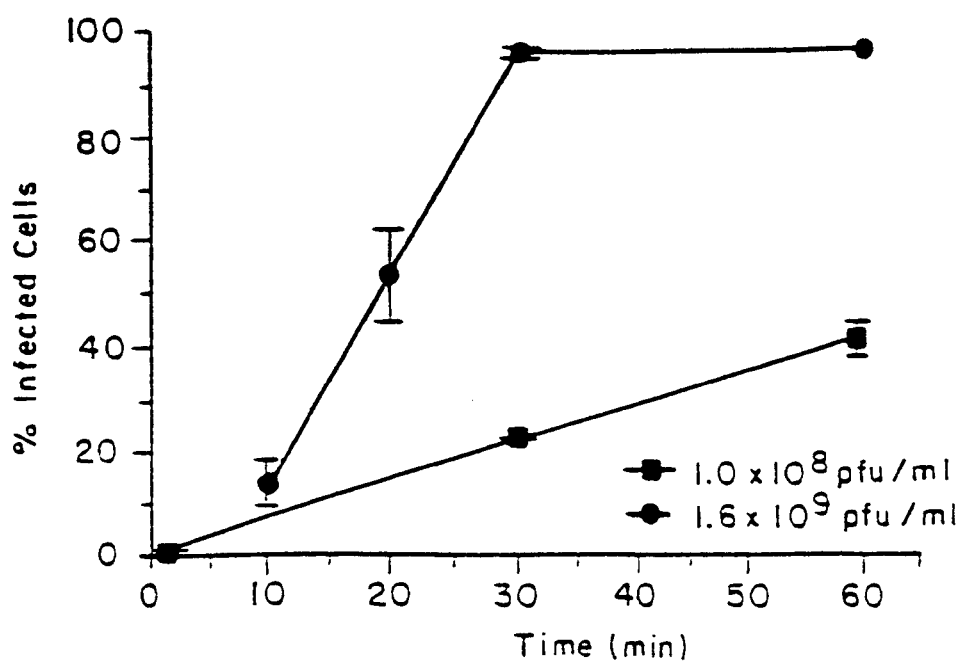
FIG. 3 shows a comparison of the time course of adenovirus infection at two virus concentrations.
Figure 4:
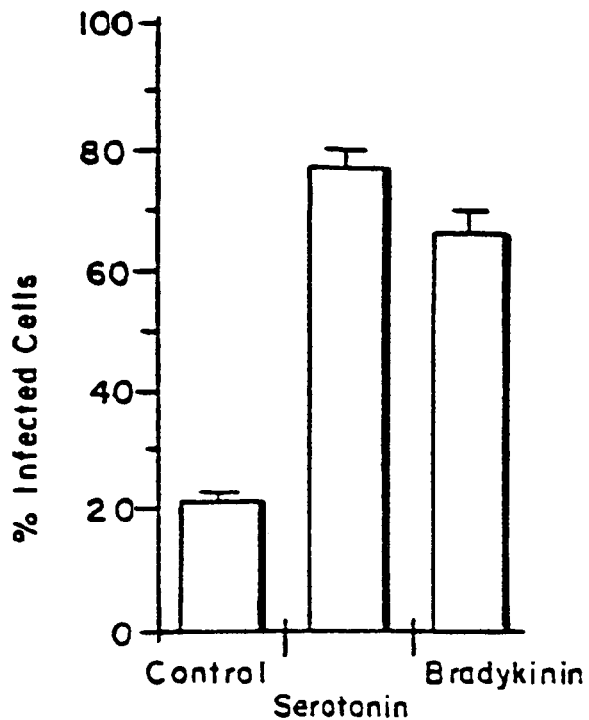
FIG. 4 shows effects on adenovirus infection after pretreatment with selected vasculature permeability agents.

Under these conditions, it was found that less than 1% of cells were infected after 2 minutes and that the percentage increased with exposure time, saturating at 40% with 60 minute infection. Increasing the virus concentration to $1.6 \times 10^9$ pfu/ml caused an improvement in both the infection rate and the final percentage of infected cells (see FIG. 3 of the drawings where results are shown; baseline conditions included infection in Krebs solution at 30 ml/min and 37° C., followed by a virus-free perfusion with Krebs solution; N=3 for each data point). The percentage of infected cells was 13.7±4.5% after 10 minutes, 52.6±8.9% at 20 minutes, and 95.3±0.7% at 30 minutes, and 96.1±0.2% after 60 minutes of virus recirculation. Each of the supplemental agents (i.e. serotonin, bradykinin and low calcium) perfused to enhance microvascular permeability caused a significant increase in the percentage of infected myocytes (see FIG. 4 of the drawings where results for serotonin and bradykinin are depicted graphically). The greatest increase occurred with exposure to serotonin, causing 77.8±2.3% infection. Bradykinin and low calcium pretreatment each resulted in 65-67% infection.

EXAMPLE 2

Combined Use of Permeability Agent and Low Calcium Concentration Conditions

Figure 5:
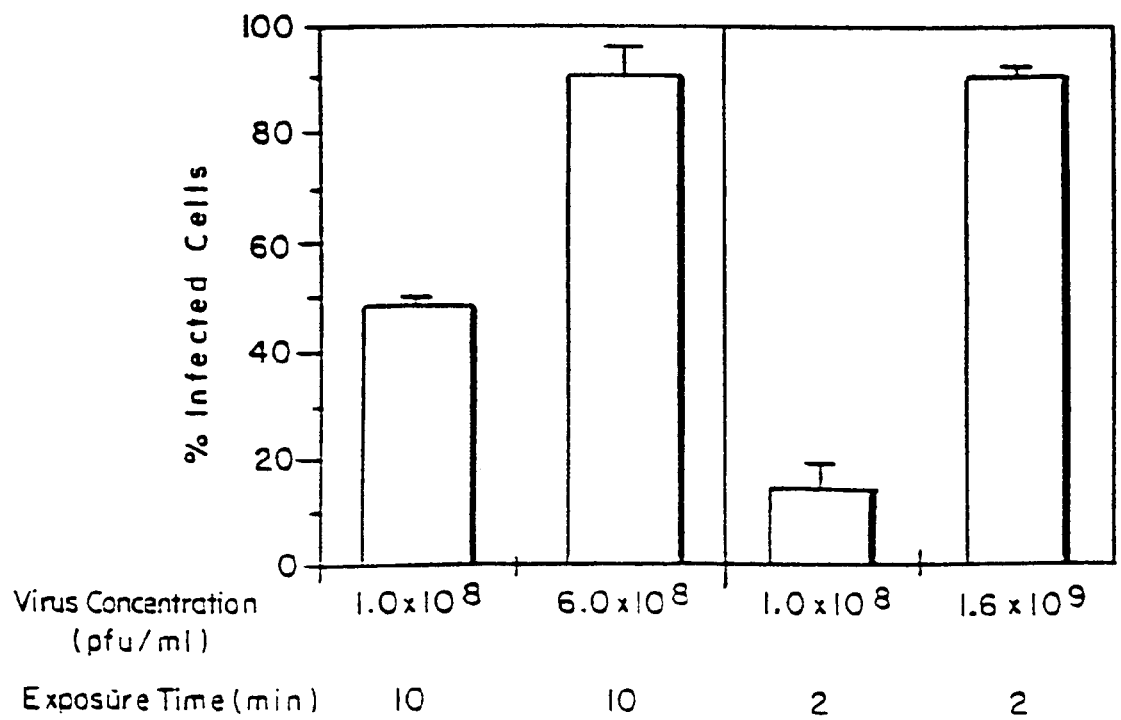
FIG. 5 shows infection rates at selected exposure times after pretreatment with a preferred vasculature permeability agent and under low calcium concentration conditions.

The serotonin and low calcium protocols as described in Example 1 above were combined. Pretreatment was accomplished with 500 ml of normal Krebs buffer containing $10^{-5}$ M of serotonin over 15 minutes followed by 90 Mlles of the same reduced calcium (50 μM) concentration solution over 3 minutes. Those same serotonin and low calcium concentration solutions were used during delivery of the Adβgal vector. Results are set forth below and in FIG. 5 of the drawings. Those results and the results of Example 1 above indicate a synergistic increase in gene transfer efficiency resulting from the combined use of a permeability agent and low calcium concentration conditions in accordance with the invention. Virus concentration was also varied to increase gene transfer efficiency. Specifically, using a virus concentration of $1.0 \times 10^8$ pfu/ml, infection occurred in 49.4±1.0% of cells after 10 minute virus exposure and 16.3±3.4% of cells after 2 minutes. Then, a ten minute exposure to an Adβgal concentration of $6.0 \times 10^8$ pfu/ml produced 91.5±4.4% infection, and an Adβgal concentration of $1.6 \times 10^9$ pfu/ml resulted in 92.3±1.0% after 2 minutes of virus exposure.

The invention has been described in detail with reference to preferred embodiments thereof. However, it will be appreciated that those skilled in the art, upon consideration of this disclosure, may make modifications and improvements within the spirit and scope of the invention.

What is claimed is:

1. A method for delivering nucleic acid to cells in a tissue of interest, comprising:

contacting the tissue with a plurality of agents which increase vascular permeability to an exogenous nucleic acid, said agents selected from the group consisting of serotonin, bradykinin, platelet-activating factor (PAF), prostaglandin $E_1$ ($PGE_1$), histamine, vascular endothelium growth factor (VEGF), zona occludens toxin (ZOT), interleukin-2, L-N-monomethyl arginine (L-NMMA), and L-N-nitro-arginine methyl ester (L-NAME); and administering to the tissue the exogenous nucleic acid under an effective amount of low calcium ion concentration of less than or equal to 500 micromolar, whereby transfer efficiency of the exogenous nucleic acid by the cells in the tissue is increased.

2. A method for delivering nucleic acid to cells in a tissue of interest, comprising:

contacting the tissue with an agent which increases vascular permeability to an exogenous nucleic acid, said agent selected from the group consisting of serotonin, bradykinin, platelet-activating factor (PAF), prostaglandin $E_1$ ($PGE_1$), histamine, vascular endothelium growth factor (VEGF), zona occludens toxin (ZOT), interleukin-2, L-N-monomethyl arginine (L-NMMA), and L-N-nitro-arginine methyl ester (L-NAME); and administering to the tissue the exogenous nucleic acid in a viral vector under an effective amount of low calcium ion concentration of less than or equal to 500 micromolar, whereby transfer efficiency of the exogenous nucleic acid by the cells in the tissue is increased.

3. A method for delivering an exogenous nucleic acid to cells of a tissue of interest, comprising:

contacting the tissue with a plurality of vascular permeability increasing agents under an effective amount of low calcium ion concentration of less than or equal to 500 micromolar to increase vascular permeability to an exogenous nucleic acid, said agents selected from the group consisting of serotonin, bradykinin, platelet-activating factor (PAF), prostaglandin $E_1$ ($PGE_1$), histamine, vascular endothelium growth factor (VEGF), zona occludens toxin (ZOT), interleukin-2, L-N-monomethyl arginine (L-NMMA), and L-N-nitro-arginine methyl ester (L-NAME); and administering the exogenous nucleic acid to the tissue, whereby transfer efficiency of the exogenous nucleic acid to the cells of the tissue of interest is increased.

4. A method for delivering an exogenous nucleic acid to cells of a tissue of interest, comprising:

contacting the tissue with a vascular permeability increasing agent under an effective amount of low calcium ion concentration of less than or equal to 500 micromolar to increase vascular permeability to an exogenous nucleic acid, said agent selected from the group consisting of serotonin, bradykinin, platelet-activating factor (PAF), prostaglandin $E_1$ ($PGE_1$), histamine, vascular endothelium growth factor (VEGF), zona occludens toxin (ZOT), interleukin-2, L-N-monomethyl arginine (L-NMMA), and L-N-nitro-arginine methyl ester (L-NAME); and administering the exogenous nucleic acid in a viral vector to the tissue, whereby transfer efficiency of the exogenous nucleic acid to the cells of the tissue of interest is increased.

5. A method for delivering a nucleic acid to malignant cells in a tissue, comprising:

treating the tissue with a plurality of vascular permeability increasing agents to increase delivery of an exogenous nucleic acid to the malignant cells in the tissue, said agents selected from the group consisting of serotonin, bradykinin, platelet-activating factor (PAF), prostaglandin $E_1$ ($PGE_1$), histamine, vascular endothelium growth factor (VEGF), zona occludens toxin (ZOT), interleukin-2, L-N-monomethyl arginine (L-NMMA), and L-N-nitro-arginine methyl ester (L-NAME); and administering to the tissue the exogenous nucleic acid under an effective amount of low calcium ion concentration of less than or equal to 500 micromolar.

6. A method for delivering a nucleic acid to malignant cells in a tissue, comprising:

treating the tissue with a vascular permeability increasing agent to increase delivery of an exogenous nucleic acid to the malignant cells in the tissue, said agent selected from the group consisting of serotonin, bradykinin, platelet-activating factor (PAF), prostaglandin $E_1$ ($PGE_1$), histamine, vascular endothelium growth factor (VEGF), zona occludens toxin (ZOT), interleukin-2, L-N-monomethyl arginine (L-NMMA), and L-N-nitro-arginine methyl ester (L-NAME); and administering to the tissue the exogenous nucleic acid in a viral vector under an effective amount of low calcium ion concentration of less than or equal to 500 micromolar.

7. A method of providing to a recipient subject donor cells that comprise nucleic acid exogenous to the cells, comprising:

contacting a tissue comprising the donor cells with a plurality of agents that increase vascular permeability to increase transfer efficiency of an exogenous nucleic acid to the donor cells, said agents selected from the group consisting of serotonin, bradykinin, platelet-activating factor (PAF), prostaglandin $E_1$ ($PGE_1$), histamine, vascular endothelium growth factor (VEGF), zona occludens toxin (ZOT), interleukin-2, L-N-monomethyl arginine (L-NMMA), and L-N-nitro-arginine methyl ester (L-NAME);

administering to the tissue comprising the donor cells nucleic acid under an effective amount of low calcium ion concentration of less than or equal to 500 micromolar; and introducing the donor cells into the recipient subject to express a gene product encoded by the nucleic acid.

8. A method of providing to a recipient subject donor cells that comprise nucleic acid exogenous to the cells, comprising:

contacting a tissue comprising the donor cells with an agent that increases vascular permeability to increase transfer efficiency of an exogenous nucleic acid to the donor cells, said agent selected from the group consisting of serotonin, bradykinin, platelet-activating factor (PAF), prostaglandin $E_1$ ($PGE_1$), histamine, vascular endothelium growth factor (VEGF), zona occludens toxin (ZOT), interleukin-2, L-N-monomethyl arginine (L-NMMA), and L-N-nitro-arginine methyl ester (L-NAME);

administering to the tissue comprising the donor cells nucleic acid in a viral vector under an effective amount of low calcium ion concentration of less than or equal to 500 micromolar; and introducing the donor cells into the recipient subject to express a gene product encoded by the nucleic acid.

9. The method of claim 7 wherein an organ comprising the donor cells is transplanted into the recipient subject.

10. The method of claim 8 wherein an organ comprising the donor cells is transplanted into the recipient subject.

11. The method of claim 7 wherein the donor cells are swine cells or primate cells.

12. The method of claim 8 wherein the donor cells are swine cells or primate cells.

13. A pharmaceutical kit comprising:

a plurality of permeability agents that can increase vascular permeability to a nucleic acid in a subject, said agents selected from the group consisting of serotonin, bradykinin, platelet-activating factor (PAF), prostaglandin $E_1$ ($PGE_1$), histamine, vascular endothelium growth factor (VEGF), zona occludens toxin (ZOT), interleukin-2, L-N-monomethyl arginine (L-NMMA), and L-N-nitro-arginine methyl ester (L-NAME), a solution having a calcium ion concentration of from about 40 µmol/L to about 500 µmol/L; and a nucleic acid for administration to a subject.

14. A pharmaceutical kit comprising:

a permeability agent that can increase vascular permeability to a nucleic acid in a subject, said agent selected from the group consisting of serotonin, bradykinin, platelet-activating factor (PAF), prostaglandin $E_1$ ($PGE_1$), histamine, vascular endothelium growth factor (VEGF), zona occludens toxin (ZOT), interleukin-2, L-N-monomethyl arginine (L-NMMA), and L-N-nitro-arginine methyl ester (L-NAME);

a solution having a calcium ion concentration of from about 40 µmol/L to about 500 µmol/L; and a nucleic acid in a viral vector for administration to a subject.

15. A treatment solution which has a calcium ion concentration of from about 40 µmol/L to about 500 µmol/L, comprising:
 a) a plurality of permeability agents that can increase vascular permeability to a nucleic acid, said agents selected from the group consisting of serotonin, bradykinin, platelet-activating factor (PAF), prostaglandin $E_1$ ($PGE_1$), histamine, vascular endothelium growth factor (VEGF), zona occludens toxin (ZOT), interleukin-2, L-N-monomethyl arginine (L-NMMA), and L-N-nitro-arginine methyl ester (L-NAME); and
 b) a nucleic acid.

16. A treatment solution which has a calcium ion concentration of from about 40 µmol/L to about 500 µmol/L, comprising:
 a) a permeability agent that can increases vascular permeability to a nucleic acid, said agent selected from the group consisting of serotonin, bradykinin, platelet-activating factor (PAF), prostaglandin $E_1$ ($PGE_1$), histamine, vascular endothelium growth factor (VEGF), zona occludens toxin (ZOT), interleukin-2, L-N-monomethyl arginine (L-NMMA), and L-N-nitro-arginine methyl ester (L-NAME); and
 b) a nucleic acid in a viral vector.

17. A treatment solution comprising a nucleic acid in a viral vector in a fluid carrier and having a calcium ion concentration of from about 40 µmol/L to about 500 µmol/L.

18. A method for delivering nucleic acid to cells in tissue of interest, comprising:
 administering to the cells an exogenous nucleic acid in a viral vector under an effective amount of low calcium ion concentration of about from about 40 µM/L to about 500 µmol/L.

19. The method of claim 18 wherein the nucleic acid is administered by perfusion.

20. The method of claim 18 wherein a perfusate of nucleic acid is recirculated and then readministered to the cells.

21. The method of claim 18 wherein a fluid having a calcium ion concentration of from about 40 µmol/L to about 500 µmol/L is used as a perfusate of the tissue.

22. The method of claim 18 wherein the cells are in a solid cell mass.

23. The method of claim 18 wherein the cells are in a solid organ.

24. The method of claim 18 wherein the cells are of an organ selected from the group consisting of heart, lung, kidney, testes, ovaries, skeletal muscle, kidneys, brain or spleen.

25. The method of claim 18 wherein the tissue is cardiac tissue.

26. The method of claim 18 wherein the tissue comprises malignant cells.

27. The method of claim 18 wherein the cells are in a solid tumor.

28. The method of claim 18 wherein the tissue is mammalian.

29. The method of claim 18 wherein the nucleic acid is administered ex vivo.

30. The method of claim 18 wherein the nucleic acid is administered in vivo.

31. The method of claim 18 wherein the nucleic acid is administered to livestock, poultry, dog or cat.

32. The method of claim 1 wherein the plurality of agents comprise VEGF.

33. The method of claim 2 wherein the viral vector is an adenovirus.

34. The method of claim 3 wherein the plurality of agents comprise VEGF.

35. The method of claim 4 wherein the viral vector is an adenovirus.

36. The method of claim 5 wherein the plurality of agents comprise VEGF.

37. The method of claim 6 wherein the viral vector is an adenovirus.

38. The method of claim 7 wherein the plurality of agents comprise VEGF.

39. The method of claim 8 wherein the viral vector is an adenovirus.

40. The pharmaceutical kit of claim 13 wherein the plurality of agents comprise VEGF.

41. The pharmaceutical kit of claim 14 wherein the viral vector is an adenovirus.

42. The treatment solution of claim 15 wherein the plurality of agents comprise VEGF.

43. The treatment solution of claim 16 wherein the viral vector is an adenovirus.

44. The treatment solution of claim 17 wherein the viral vector is an adenovirus.

45. The method of claim 18 wherein the viral vector is an adenovirus.

46. The method of claim 19 wherein the viral vector is an adenovirus.

47. The method of claim 20 wherein the viral vector is an adenovirus.

48. The method of claim 21 wherein the viral vector is an adenovirus.

49. The method of claim 32 wherein the exogenous nucleic acid is in a viral vector.

50. The method of claim 34 wherein the exogenous nucleic acid is in a viral vector.

51. The method of claim 36 wherein the exogenous nucleic acid is in a viral vector.

52. The method of claim 38 wherein the exogenous nucleic acid is in a viral vector.

53. The method of claim 32 wherein the exogenous nucleic acid is in a adenoviral vector.

54. The method of claim 34 wherein the exogenous nucleic acid is in a adenoviral vector.

55. The method of claim 36 wherein the exogenous nucleic acid is in a adenoviral vector.

56. The method of claim 38 wherein the exogenous nucleic acid is in a adenoviral vector.

57. The pharmaceutical kit of claim 40 wherein the nucleic acid is in a viral vector.

58. The pharmaceutical kit of claim 40 wherein the nucleic acid is in adenoviral vector.

59. The treatment solution of claim 42 wherein the nucleic acid is in a viral vector.

60. The treatment solution of claim 42 wherein the nucleic acid is in adenoviral vector.

* * * * *